(12) United States Patent
Crawford et al.

(10) Patent No.: US 6,589,526 B2
(45) Date of Patent: Jul. 8, 2003

(54) ENRICHMENT OF DENDRITIC CELLS FROM BLOOD

(75) Inventors: Keith D. Crawford, Boston, MA (US); Chester A. Alper, Brookline, MA (US)

(73) Assignee: Center for Blood Research, Boston, MA (US)

( * ) Notice: Subject to any disclaimer, the term of this patent is extended or adjusted under 35 U.S.C. 154(b) by 185 days.

(21) Appl. No.: 09/774,948

(22) Filed: Jan. 31, 2001

(65) Prior Publication Data

US 2001/0023072 A1 Sep. 20, 2001

Related U.S. Application Data (62) Division of application No. 08/902,246, filed on Jul. 29, 1997, now Pat. No. 6,194,204.
(60) Provisional application No. 60/023,028, filed on Aug. 2, 1996.

(51) Int. Cl.$^7$ ................................................. C12N 5/06
(52) U.S. Cl. ....................... 424/93.71; 424/530; 424/534
(58) Field of Search ................... 435/372; 424/93.71, 424/530, 534

(56) References Cited

U.S. PATENT DOCUMENTS

| | | | |
|---|---|---|---|
| 5,395,688 A | 3/1995 | Wang et al. | ................ 428/327 |
| 5,643,786 A | 7/1997 | Cohen et al. | ................ 435/325 |
| 5,648,219 A | 7/1997 | MacKay et al. | ................ 935/6 |

FOREIGN PATENT DOCUMENTS

| WO | WO95/34638 | 12/1995 |
|---|---|---|

OTHER PUBLICATIONS

Richardson, The End of the Self, Discover, pp. 80–87 (Apr., 1996).
Hsu et al., Vaccination of patients with B–cell lymphoma using autologous antigen–pulsed dendritic cells, Nature 2:52–59 (1996).
Karhumaki et al., An improved enrichment method for functionally competent, highly purified peripheral blood dendritic cells and its application to HIV–infected blood samples, Clin. Exp. Immunol. 91:482–488 (1993).
Thomas et al., Isolation and Characterization of Human Peripheral Blood Dendritic Cells, J. of Immunology 150:821–834 (1993).
Inaba et al., Generation of Large Numbers of Dendritic Cells from Mouse Bone Marrow Cultures Supplemented with Granulocyte/Macrophage Colony–stimulating Factor, J. Exp. Med. 176:1693–1702 (1992).
Miltenyi et al., High Gradient Magnetic Cell Separation with MACS, Cytometry 11:231–238 (1990).
Arulanandam and Reinherz, T11.1 Epitope mapping of Workshop anti–CD2 mAb using human CD2 adhesion domain mutants derived by site–directed mutagenesis, Leucocyte Typing V, Antigens, White Cell Differentiation Schlossman et al., editor, Oxford University Press, vol. 1, pp. 344–345 (1995).
Zhou et al., A Novel Cell–Surface Molecule Expressed by Human Interdigitating Reticulum Cells, Langerhans Cells, and Activated Lymphocytes is a New Member of the Ig Superfamily, J. Immunol. 149:735–742 (1992).

(List continued on next page.)

*Primary Examiner*—Jean C. Witz
(74) *Attorney, Agent, or Firm*—Ropes & Gray, LLP (57) ABSTRACT

A method for the enrichment of dendritic cells from the peripheral blood of a mammal is described. Peripheral blood having mononuclear cells from a mammal is provided. The mononuclear cells are separated from the peripheral blood. The mononuclear cells are separated into a first cell population having substantially lymphocytes and a second cell population having substantially myeloid cells. The myeloid cells are separated into a third cell population having substantially monocytes and a fourth cell population having substantially dendritic cells. Also described are purified dendritic cell populations, vaccine compositions and methods for the treatment of cancer using dendritic cells, and kits useful for the enrichment of dendritic cells from blood.

48 Claims, 1 Drawing Sheet

OTHER PUBLICATIONS

Triglia et al., Rapid Changes in Surface Antigen Expression by Blood Monocytes Cultured in Suspension or Adherent to Plastic, Blood 65:921–928 (1985).

Denning. S., T11 CD2 cluster report, Leucocyte Typing V, White Cell Differentiation Antigens, Schlossman et al., editor, Oxford University Press, vol. 1, pp. 342–343 (1995).

Siliciano et al., Activation of cytolytic T lymphocyte and natural killer cell function through the T11 sheep erythrocyte binding protein, Nature 317:428–430 (1985).

O'Doherty et al., Dendritic Cells Freshly Isolated from Human Blood Express CD4 and Mature into Typical Immunostimulatory Dendritic Cells after Culture in Monocyte-conditioned Medium, J. Exp. Med. 178:1067–1078 (1993).

Zhou and Tedder, Human Blood Dendritic Cells Selectively Express CD83, A Member of the Immunoglobulin Superfamily, J. of Immunol. 154:3821–3835 (1995).

Crawford et al., A novel lymphocyte restricted antigen which is exclusively expressed by human circulating dendritic leukocytes, Blood 80(10) Suppl. 1:192a (1992).

Bowden et al., T11.2 Epitopes and functional responses defined by Workshop anti–CD2 mAb, Leucocyte Typing V, Antigens, White Cell Differentiation, Schlossman ed. Oxford University Press, vol. 1, pp. 346–347 (1995).

Reinherz et al., The Biology of Human CD2, Cold Spring Harbor Symposia on Quantitative Biology, vol. LIV, 611–625 (1989).

Barclay et al., The Leucocyte Antigen Facts Book, Academic Press, pp. 104–113, 116–119, 124–127, 136–137, 142–145, 154–155, 228–229 (1993).

Arulanandam et al., The CD58 (LFA–3) binding site is a localized and highly charged surface area on the AGFCC'C" face of the human CD2 adhesion domain, PNAS USA 90:11613–11617 (1993).

Caux et al., Recent advances in the study of dendritic cells and follicular dendritic cells, Immunology Today, 16(1):2–4 (1994).

Coulter Immunology, 440 West 20th Street, Hialeah, FL 33010, Coulter Clone® T11, T11–RD1, T11–FITC Monoclonal Antibody for In Vitro Diagnostic Use, pp. 1, 2, 5–7.

Coulter Corporation, 11800 S.W. 147th Avenue, Miami FL 33196–2500, Coulter Clone® T11, T11–RD1, T11–FITC Monoclonal Antibody for In Vitro Diagnostic Use.

Coulter Corporation, 11800 S.W. 147th Avenue, Miami, FL 33196–2500, Cyto–Stat®/Coulter Clone® T11, T11–RD1, T11–FITC Monoclonal Antibody for In Vitro Diagnostic Use.

Coulter Corporation, 11800 S.W. 147th Avenue, Miami, FL 33196–2500, Coulter Clone® MY4, MY4–RD1, MY4–FITC Monoclonal Antibody for In Vitro Diagnostic Use.

Becton Dickinson Immunocytometry Systems, 2350 Qume Drive, San Jose, CA 95131–1807, Monoclonal Antibodies Detecting Human Antigens, CD5 (Leu™–1), Source Book Section 4.1.1–4.1.3, 1993.

Becton Dickinson Immunocytometry Systems, 2350 Qume Drive, San Jose, CA 95131–1807, Monoclonal Antibodies Detecting Human Antigens, CD14 (Leu™–M3), Source Book Section 4.25.1–4.25.2, 1993.

Miltenyi Biotec, Inc., 251 Auburn Ravine Road, Suite 208, Auburn, CA 95603, MACS Cell Isolation Kit, Blood Dendritic Cell Isolation Kit, section 14.4, Appendix.

Miltenyi Biotec GmbH, Friedrich–Ebert –Strasse 68, 51429 Bergisch Gladbach, Germany—Press Release—New MACS Blood Dendritic Cell Isolation Kit, Cologne, Germany, Aug. 31, 1995.

Miltenyi Biotec GmbH, Friedrich–Ebert–Strasse 68, 51429 Bergisch Gladbach, Germany—Magnetic Cell Separation of Human Leucocytes (CD3 Microbeads, CD4 Microbeads, CD8 Microbeads, CD14 Microbeads, CD16 Microbeads, CD19 Microbeads, Rat anti–mouse IgG1 Microbeads and Rat anti–mouse IgG2a+b).

Miltenyi Biotec, Inc., 1250 Oakmead Park, Suite 210, Sunnyvale, CA 94088–3599—MACS Cell Separation Reagents for Human Cells, pp. 3.7, 3.10, 3.12, 3.13, 5.1.

Miltenyi Biotec GmbH, Friedrich–Ebert–Strasse 68, 51429 Bergisch Gladbach, Germany—Blood Dendritic Cell Isolation Kit.

ENRICHMENT OF DENDRITIC CELLS FROM BLOOD

This application is a division of application Ser. No. 08/902,246, filed Jul. 29, 1997, now U.S. Pat. No. 6,194,204, which claims the benefit of U.S. Provisional Application No. 60/023,028 filed Aug. 2, 1996.

The U.S. Government has a paid-up license in this invention and the right in limited circumstances to require the patent owner to license others on reasonable terms as provided for by the terms of Grant No. 5 P01HL29583 awarded by the National Institutes of Health.

FIELD OF THE INVENTION

This invention relates to a method for the enrichment of dendritic cells from the peripheral blood of a mammal, to purified dendritic cell populations, and to kits useful for enrichment of dendritic cells.

BACKGROUND OF THE INVENTION

Dendritic cells are antigen-presenting cells that are found in all tissues and organs, including the blood. Specifically, dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph for an injury signal (e.g., ischemia, infection, or inflammation) or tumor growth. Once signaled, dendritic cells initiate the immune response by releasing IL-1 which triggers lymphocytes and monocytes.

Dendritic cells can play either a positive or negative role in various immunologically related situations. For example, dendritic cells are thought to be involved in transplant rejection and autoimmune diseases, and it may be desirable to block their function in such situations. On the other hand, various immunodeficiencies, e.g., towards tumors, may result from deficient dendritic cells. In addition, there is evidence that HIV can infect certain populations of dendritic cells.

It is desirable to obtain substantially pure populations of dendritic cells, e.g., in order to exploit the important role of dendritic cells in various immunotherapies. Dendritic cell isolation is particularly difficult, however, because it is believed that they are very low in frequency in blood and other tissues, and because there is no reported surface marker expressed by fresh and cultured dendritic cells which distinguishes it from monocytes. Conventional methods for isolation which enrich subpopulations of cell mixtures include, e.g., density gradient separation, fluorescence activated cell sorting, immunological cell separation techniques such as panning, complement lysis, rosetting, magnetic cell separation techniques, and nylon wool separation. Different patterns of expression of cell surface antigens have been used in some cases to identify different cell types. Certain disadvantages of many of these reported methods are that they can be time-consuming, labor-intensive, costly, require large amounts of reagent, can result in low specificity, low sensitivity, contaminated mixtures, poor and/or inaccurate separation, loss of desired cells, or can change the properties, functions, or viability of the desired cells. Thus, prior methods generally are inefficient, time-consuming, expensive and do not optimize for pure populations.

SUMMARY OF THE INVENTION

It is an object of the invention to provide an easy, effective, and inexpensive method for isolating dendritic cells from tissue, e.g., peripheral blood, of a mammal.

It is yet another object of the invention to provide a method for isolating dendritic cells which are viable and substantially unaltered in cell function.

It is yet another object of the invention to provide a method for isolating dendritic cells which are substantially pure.

It is yet another object of the invention to provide a method for isolating dendritic cells which can be used in various immunotherapeutic regimens.

It is yet another object of the invention to provide a method for isolating dendritic cells which express high levels of CD14.

It is yet another object of the invention to provide a method for isolating dendritic cells from monocytes.

It is yet another object of the invention to provide a method for isolating dendritic cells from tissue, e.g., peripheral blood, of a mammal which are unactivated.

Still another object of the invention is to provide a method for isolating monocytes from the tissue, e.g., peripheral blood, of a mammal which are unactivated.

According to the invention, a method for the enrichment of dendritic cells from the peripheral blood of a mammal is provided. Peripheral blood having mononuclear cells from a mammal is provided, and the mononuclear cells are separated from the peripheral blood. These mononuclear cells are separated into a first cell population having substantially lymphocytes, e.g., T cells, NK cells, B cells or mixtures thereof, and a second cell population having substantially myeloid cells. These myeloid cells are separated into a third cell population having substantially monocytes and a fourth cell population having substantially dendritic cells.

In certain embodiments, the separation of the mononuclear cells into a first cell population having substantially lymphocytes and a second cell population having substantially myeloid cells comprises contacting the mononuclear cells with antibodies against the lymphocytes so as to form an antibody-lymphocyte complex, and selectively separating the antibody-lymphocyte complex from the myeloid cells. The antibodies used, e.g., monoclonal antibodies, are directed against one or more antigens which are expressed by one or more of the lymphocytes. For example, T cell antibodies include anti-CD3 antibodies, anti-CD8 antibodies, and mixtures thereof; NK cell antibodies include, e.g., anti-CD16/56 antibodies; and B cell antibodies include, e.g., anti-CD19 or anti-CD20 antibodies.

In certain embodiments, the antibody-lymphocyte complex that is formed is selectively separated from the myeloid cells by contacting the antibody-lymphocyte complex and the myeloid cells with a matrix such that the antibody-lymphocyte complex is substantially retained by the matrix, e.g., greater than 20%, 40%, 60%, 80%, 90%, 95%, 98%, or 99% retained, and the myeloid cells are substantially not retained by the matrix, e.g., greater than 20%, 40%, 60%, 80%, 90%, 95%, 98%, or 99% not retained.

Preferably, the antibody-lymphocyte complex further comprises magnetic beads, e.g., superparamagnetic microparticles. The magnetic beads can be attached, e.g., to the antibody or to the lymphocyte or to both. In embodiments in which the antibody-lymphocyte complex has magnetic beads, separation of such a complex from the myeloid cells preferably comprises contacting the myeloid cells and the complex with a magnetic matrix, e.g., magnetized steel wool, such that the antibody-lymphocyte complex having the magnetic beads is substantially retained by the magnetic matrix and the myeloid cells are substantially not retained by the magnetic matrix.

A variation of this method is separating the mononuclear cells into a first cell population having substantially lymphocytes and a second cell population having substantially myeloid cells by centrifugation, e.g., density gradient centrifugation.

In certain embodiments, the separation of the mononuclear cells into a third cell population having substantially monocytes and a fourth cell population having substantially dendritic cells comprises contacting the myeloid cells with antibodies against the dendritic cells so as to form an antibody-dendritic cell complex, and selectively separating the antibody-dendritic cell complex from the monocytes. The antibodies used, e.g., monoclonal antibodies, are directed against one or more antigens which are expressed by the dendritic cells, e.g., anti-CD2 antibodies, anti-CD5 antibodies or mixtures thereof. In certain embodiments, the myeloid cells are cultured prior to contacting the myeloid cells with the antibodies, and anti-CD83 antibodies are used.

In certain embodiments, the antibody-dendritic cell complex that is formed is selectively separated from the monocytes by contacting the antibody-dendritic cell complex and the monocytes with a matrix such that the antibody-dendritic cell complex is substantially retained by the matrix and the monocytes are substantially not retained by the matrix. Preferably, the retained antibody-dendritic cell complex is then eluted from the matrix.

Preferably, the antibody-dendritic cell complex further comprises magnetic beads. In such embodiments, separation of the antibody-dendritic complex from the monocytes preferably comprises contacting the monocytes and the antibody-dendritic cell complex having the magnetic beads with a magnetic matrix such that the antibody-dendritic cell complex having the magnetic beads is substantially retained by the magnetic matrix and the monocytes are substantially not retained by the magnetic matrix. Preferably, the retained antibody-dendritic cell complex is then eluted from the matrix, e.g., by demagnetizing the matrix, e.g., by removing the matrix from the magnetic field.

Preferably, the dendritic cells in the fourth cell population are greater than about 60%, 70%, 80%, 90%, 95% 98%, or 99% pure. Preferably, the monocytes in the third cell population are greater than about 70%, 80%, 90%, 95%, 98%, or 99% pure. Preferably, the monocytes in the third cell population and/or the dendritic cells in the fourth cell population are substantially unactivated.

Other aspects of the invention are enriching for dendritic cells from the peripheral blood mononuclear cells or from the myeloid cells of a mammal.

Another aspect of the invention is a method for the enrichment of dendritic cells from the peripheral blood of a mammal comprising selecting cells from the peripheral blood which do not express antigens CD3, CD16/56 and CD19 or CD20, and which do express antigen CD2, CD5, CD83, or mixtures thereof, and which preferably, also express antigen CD14.

The invention also includes a method for the enrichment of dendritic cells from tissue of a mammal. Tissue having mononuclear cells from a mammal is provided. The mononuclear cells are separated from the tissue. The mononuclear cells are separated into a first cell population having substantially lymphocytes and a second cell population having substantially myeloid cells. The myeloid cells are separated into a third cell population having substantially monocytes and a fourth cell population having substantially dendritic cells.

Another aspect of the invention is the products obtained from the above described methods.

Another aspect of the invention is a substantially purified population of mammalian dendritic cells, e.g., greater than about 80%, 90%, 95%, 98%, or 99% pure, in which the dendritic cells express antigen CD14. In certain embodiments, the dendritic cells also express antigen CD2 and/or CD5 and/or CD83.

Another aspect of the invention is a kit useful for enriching for dendritic cells from blood. The kit includes, e.g., anti-CD2 antibodies, anti-CD5 antibodies, anti-CD83 antibodies, or mixtures thereof, and lymphocyte antibodies. The lymphocytes include, e.g., T cells, NK cells, B cells and mixtures thereof. Preferably, the T cell antibodies include anti-CD3 antibodies, anti-CD8 antibodies, or mixtures thereof; the NK cell antibodies include, e.g., anti-CD16/56 antibodies; and the B cell antibodies include, e.g., anti-CD19 or anti-CD20 antibodies.

Variations include, e.g., the kit also having magnetic beads, e.g., superparamagnetic microparticles, which are either complexed to the antibodies or are separate. Other variations include the kit having matrix material, preferably provided in a column, and preferably capable of being magnetized by exposure to a magnetic field, e.g., the matrix can be steel wool.

Another aspect of the invention is a vaccine composition for treating cancer in a mammal comprising a therapeutically effective amount of dendritic cells wherein the dendritic cells express antigen CD14. In certain embodiments, the dendritic cells are treated with cancer-specific antigen so as to stimulate host immunity to the cancer when the vaccine composition is administered to a mammal.

Yet another aspect of the invention is a method for treating a mammal for cancer. A mammal in need of treatment for cancer is provided. A vaccine composition comprising a therapeutically effective amount of dendritic cells wherein the dendritic cells express antigen CD14, is provided. The vaccine composition is administered to the mammal such that treatment of the cancer occurs.

Earlier methods for the preparation of dendritic cells have depended on the beliefs that monocytes are $CD14^+$, $CD11b^+$, $CD18^+$, whereas dendritic cells are $CD14^-$, $CD11b^-$, $CD18^-$, or in the case of CD14, dim and much lower than monocytes, and that both cell populations are $CD2^-$ and $CD5^-$. These earlier methods generally yield purified preparations of dendritic cells that represent about 0.1–0.3% of peripheral blood mononuclear cells. This invention, however, indicates that freshly isolated dendritic cells express high levels of CD2, CD5, CD14, CD11b and CD18, whereas freshly isolated monocytes express only high levels of CD14, CD11b and CD18, and do not express either CD2 or CD5. Furthermore, CD14, CD11b and CD18 are down-regulated or lost on incubation of dendritic cells, particularly in the universally used fetal calf serum as medium additive.

This invention is partially based on the fact that certain low density mononuclear cells are largely $CD33^+$ monocytes and dendritic cells. As with prior methods, contaminating T cells, B cells and NK cells are removed with anti-CD3, anti-CD20 and anti-CD16 antibodies. In the new method of this current invention, anti-CD2 (or anti-CD5) beads are used to positively select dendritic cells. In addition, the culturing is performed in pooled human serum rather than fetal calf serum to avoid activation. The purified dendritic cells exhibit greater mixed lymphocyte reactivity and express higher amounts of class II MHC antigens than purified monocytes, show typical dendritic cell morphology on electron microscopy, and react with X-11 and anti-CD83, antibodies that react with dendritic cells but not monocytes.

The advantages of the invention include, e.g., (i) greater yield (up to about 30-fold greater) compared with prior methods; (ii) greater purity of the dendritic cells (>95% compared with about 50–60% using prior methods); (iii) more representative population of dendritic cells than obtained from prior methods; (iv) the ability to isolate non-activated dendritic cells capable of all functions, which is not possible with previous methods; (v) much shorter time for isolation (about 75 minutes vs. about 5–36 hours with prior methods); and (vi) applicable to skin, lymph nodes and other tissues.

The above and other objects, features and advantages of the present invention will be better understood from the following specification when read in conjunction with the accompanying drawings.

DETAILED DESCRIPTION

Figure 1:
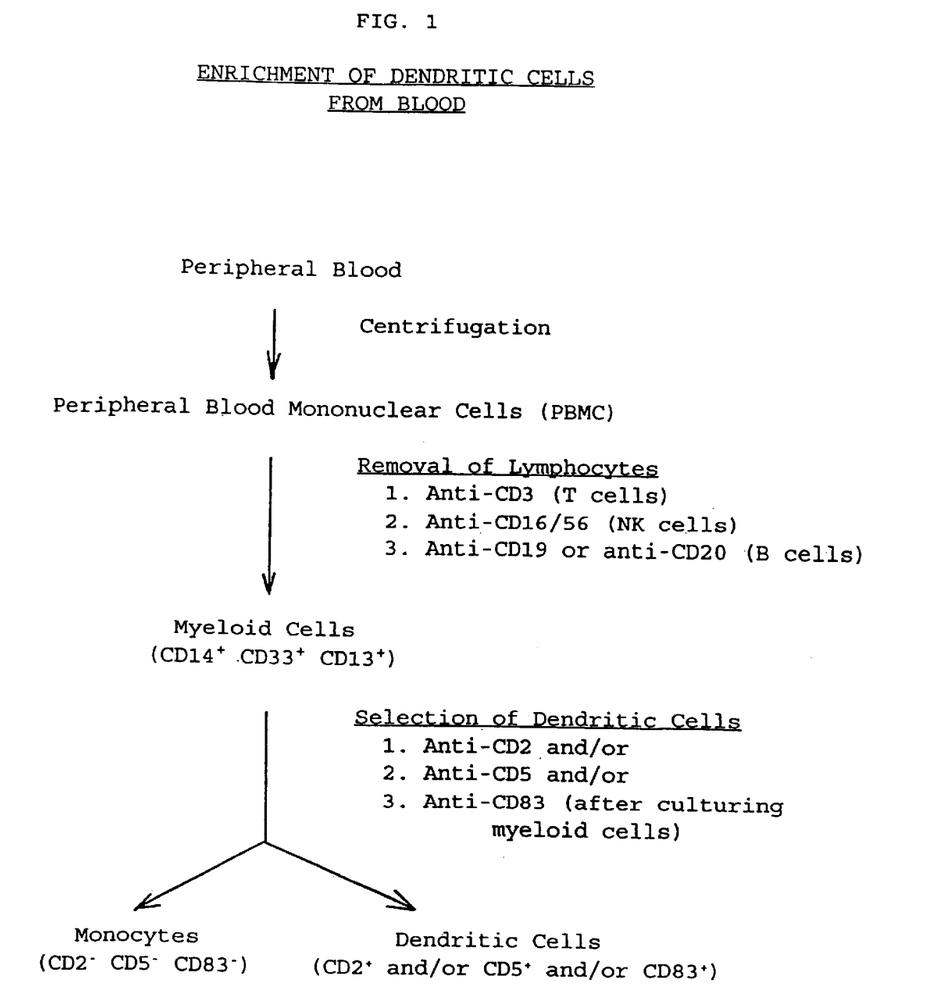
FIG. 1 is a flow-chart for enrichment of dendritic cells from blood according to an embodiment of this invention.

This invention provides a method for the enrichment of dendritic cells from the peripheral blood of a mammal. Peripheral blood having mononuclear cells from a mammal is provided. The mononuclear cells are separated from the peripheral blood. These mononuclear cells are separated into a first cell population having substantially lymphocytes and a second cell population having substantially myeloid cells. These myeloid cells are separated into a third cell population having substantially monocytes and a fourth cell population having substantially dendritic cells. FIG. 1 is a flowchart which illustrates an embodiment of this invention.

By peripheral blood is meant blood found in the circulation vasculature. The peripheral blood can be obtained from any mammal. By mammal is meant human as well as non-human mammal. A preferred non-human mammal is a pig. The mononuclear cells can be separated from the peripheral blood by any method known to those skilled in the art. Preferably, the method used does not affect cell function or viability. A preferred method is the use of centrifugation, preferably density gradient centrifugation, preferably discontinuous density gradient centrifugation. An alternative is the use of specific monoclonal antibodies.

In certain embodiments, the invention provides a method for the enrichment of dendritic cells in which the starting material is either mononuclear cells from peripheral blood or myeloid cells, rather than the peripheral blood itself.

The mononuclear cells are separated into a first cell population having substantially lymphocytes and a second cell population having substantially myeloid cells. Lymphocytes are meant to include, e.g., T cells, NK cells, B cells and mixtures thereof. By a cell population having substantially lymphocytes is meant that the cell population has greater than about 20% lymphocytes, preferably greater than about 40% lymphocytes, more preferably greater than about 60% lymphocytes, more preferably yet greater than about 80% lymphocytes, more preferably yet greater than about 90% lymphocytes, more preferably yet greater than about 95% lymphocytes, more preferably yet greater than about 98% lymphocytes, and most preferably greater than about 99% lymphocytes. Myeloid cells are meant to include monocytes and dendritic cells. Monocytes are also meant to include macrophages. It is known that monocytes circulate in the peripheral blood, and when they migrate to the tissue, they are called macrophages. This lineage of cells are commonly called monocyte/macrophage lineage. Myeloid cells are generally $CD14^+$, $CD33^+$ and $CD13^+$. By a cell population having substantially myeloid cells is meant that the cell population has greater than about 20% myeloid cells, preferably greater than about 40% myeloid cells, more preferably greater than about 60% myeloid cells, more preferably yet greater than about 80% myeloid cells, more preferably yet greater than about 90% myeloid cells, more preferably yet greater than about 95% myeloid cells, more preferably yet greater than about 98% myeloid cells, and most preferably greater than about 99% myeloid cells.

In certain embodiments, the separation of the mononuclear cells into a first cell population having substantially lymphocytes and a second cell population having substantially myeloid cells comprises contacting the mononuclear cells with antibodies against the lymphocytes so as to form an antibody-lymphocyte complex, and selectively separating the antibody-lymphocyte complex from the myeloid cells. One or more than one type of antibody can be used. In certain embodiments, the contacting and the selectively separating steps are repeated. These steps can be repeated using the same type of antibody or antibodies against the lymphocytes, or they can be repeated using a different type of antibody or antibodies against the lymphocytes.

Both polyclonal and monoclonal antibodies can be used in this invention. Preferably, monoclonal antibodies are used. Antibodies against the lymphocytes include, e.g., T cell antibodies, NK cell antibodies, B cell antibodies, or mixtures thereof. Preferably, mixtures of the antibodies are used. The antibodies used are directed against one or more antigens which are expressed by one or more of the lymphocytes.

Preferably, the T cell antibodies are anti-CD3 antibodies. All T cells express the CD3 surface molecule. CD3 is described in Barclay et al., The Leukocyte Antigen Facts Book, Academic Press Limited (1993), pp. 106–109. Anti-CD3 antibodies can be obtained from Becton Dickinson Immunocytometry Systems, San Jose, Calif. or Coulter Corp., Miami, Fla. Other T cell antibodies that can be used include, e.g., anti-CD8 antibodies. CD8 is described in Barclay et al., The Leukocyte Antigen Facts Book, Academic Press Limited (1993), pp. 118–119. Anti-CD8 antibodies can be obtained from Becton Dickinson Immunocytometry Systems or Coulter Corp. Not all T cells express CD8. CD8 is expressed by roughly 40% of the T-lymphocyte population. Therefore, using, e.g., anti-CD8 antibodies will generally not result in the separation of the entire T cell population from the myeloid cells. There are, however, certain situations in which it might be desirable to use anti-CD8 antibodies. For example, $CD8^+$ T lymphocytes represent a cytotoxic T-lymphocyte population. This population selectively targets and kills cells which were exposed to pathogen-specific antigens used in the production of pathogen-specific cytotoxic T cell lysis (intracellular pathogens).

Preferably, the NK cell antibodies are anti-CD16/56. CD16/56 refers to CD16 and CD56; they are not the same antigen, but are both expressed by NK cells. ($CD8^+$ T lymphocytes also express CD16). Anti-CD16/56 antibodies can be obtained from Becton Dickinson Immunocytometry Systems or Coulter Corp. In certain embodiments, the NK cell antibodies can be anti-CD8. Not all NK cells express CD8, and therefore using anti-CD8 antibodies will not result in the separation of the entire NK cell population from the myeloid cells.

Preferably, the B cell antibodies are anti-CD19 or anti-CD20 antibodies. CD19 and CD20 are expressed by resting and activated B lymphocytes. CD19 and CD20 are described in Barclay et al., The Leukocyte Antigen Facts Book, Academic Press Limited (1993), pp. 142–143 and 144–145, respectively. Anti-CD19 and anti-CD20 antibodies can be obtained from Becton Dickinson Immunocytometry Systems or Coulter Corp.

The antibody-lymphocyte complex that is formed is selectively separated from the myeloid cells. In certain embodiments, this separation comprises contacting the antibody-lymphocyte complex and the myeloid cells with a matrix such that the antibody-lymphocyte complex is substantially retained by the matrix and the myeloid cells are substantially not retained by the matrix. Any matrix which performs such a separation can be used.

A matrix which is particularly useful is a mesh of steel wool which is inserted into a plastic column and placed in a magnetic field. A cell magnetic bead complex passes into the matrix and remains in the matrix as long as the column stays within the magnetic field. Examples of matrices include depletion columns type BS, type CS, type D RS+, and MS+ used for Mini Mags separator. (All these columns can be obtained from Miltenyi Biotec, Auburn, Calif.) Preferably, the matrix is provided in a column, though the matrix can be provided in any other way known to those skilled in the art, e.g., in a gel, on a filter, on a plate, on film or on paper.

By the complex being substantially retained by the matrix is meant that greater than about 20% of the complex is retained, preferably greater than about 40% is retained, more preferably greater than about 60% is retained, more preferably yet greater than about 80% is retained, more preferably yet greater than about 90% is retained, more preferably yet greater than about 95% is retained, and most preferably greater than about 98% is retained. By the myeloid cells being substantially not retained by the matrix is meant that greater than about 20% of the myeloid cells are not retained, preferably greater than about 40% are not retained, more preferably greater than about 60% are not retained, more preferably yet greater than about 80% are not retained, more preferably yet greater than about 90% are not retained, more preferably yet greater than about 95% are not retained, and most preferably greater than about 98% are not retained.

In preferred embodiments, the antibody-lymphocyte complex further comprises magnetic beads. Preferably, the magnetic beads are superparamagnetic microparticles, though any type of magnetic bead can be used. The magnetic beads can be attached, e.g., to the antibody or to the lymphocyte or to both. Preferably, the magnetic beads are attached to the antibody. Such attached antibodies can be obtained, e.g., from Miltenyi Biotec, Auburn, Calif. (as MACS superparamagnetic microbeads conjugated with monoclonal antibodies), or from Dynal Corp., Lake Success, N.Y. (as detachable or non-detachable large magnetic beads). See also Miltenyi et al., *Cytometry* 11:231–238 (1990). Preferably, the large magnetic beads (obtainable from Dynal Corp.), are used for the removal of lymphocytes. Preferably, the smaller beads (obtainable from Miltenyi Biotec), are used for the enrichment of the dendritic cells described below. The magnetic beads can be attached prior to the formation of the antibody-lymphocyte complex, or subsequent to the formation of the complex. Preferably, the magnetic beads are attached prior to formation of the complex.

In embodiments in which the antibody-lymphocyte complex has magnetic beads, separation of such a complex from the myeloid cells preferably comprises contacting the myeloid cells and the complex with a magnetic matrix such that the antibody-lymphocyte complex having the magnetic beads is substantially retained by the magnetic matrix and the myeloid cells are substantially not retained by the magnetic matrix. An example of a magnetic matrix is magnetized steel wool. Steel wool can be obtained from Miltenyi Biotec. The steel wool can be magnetized by, e.g., introducing it into a magnetic field, e.g., 0.6 Tesla, though other strength magnetic fields can also be used as known to those skilled in the art. The magnetic field can be produced, e.g., with a commercial electromagnet.

In certain embodiments, the antibodies to the T cells, NK cells and B cells are all contacted with the mononuclear cells prior to selectively separating the resulting antibody-lymphocyte complexes from the myeloid cells. In other embodiments, antibodies to only one type of lymphocyte cell are added (e.g., T cells), and the resulting antibody-lymphocyte complex is separated from the remaining cells. Antibodies to one of the remaining types of lymphocytes (e.g., NK cells) are then added to the remaining cells from above, and the resulting antibody-lymphocyte complex is separated from these remaining cells. Finally, antibodies to the remaining type of lymphocyte (e.g., B cells) are then added to this second batch of remaining cells, and the resulting antibody-lymphocyte complex is separated from these remaining cells (predominantly the myeloid cells). Preferably, all of the antibodies are added prior to selective separation.

The invention also includes embodiments in which separation of the mononuclear cells into a first cell population having substantially lymphocytes and a second cell population having substantially myeloid cells, comprises centrifugation. The centrifugation can be, e.g., density gradient centrifugation. For example, metrizamide 14.5% (obtained from Sigma Chemical Co., St. Louis, Mo.) or Monocyte 1 step (which is a pre-made discontinuous gradient which separates lymphocytes from myeloid cells, obtained from Accurate Chemical and Scientific Corp., Westbury, N.Y.), can be used. Centrifugation procedures are most useful if there are initially a large number of PBMCS, e.g., about $10^9$.

In certain embodiments, the separation of the mononuclear cells into a third cell population having substantially monocytes and a fourth cell population having substantially dendritic cells comprises contacting the myeloid cells with antibodies against the dendritic cells so as to form an antibody-dendritic cell complex, and selectively separating the antibody-dendritic cell complex from the monocytes. In certain embodiments, the contacting and the selectively separating steps are repeated. These steps can be repeated using the same type of antibody or antibodies against the dendritic cells, or they can be repeated using a different type of antibody or antibodies against the dendritic cells.

Preferably, monoclonal antibodies are used. The antibodies used are directed against one or more antigens which are expressed by the dendritic cells. Preferably, the antibodies are anti-CD2 antibodies, anti-CD5 antibodies, or mixtures thereof. Most preferably, anti-CD2 antibodies are used because they stain greater than 95% of the dendritic cells and do not modulate down in culture. Mixtures of the antibodies can also be used. CD2 and CD5 are described in Barclay et al., The Leukocyte Antigen Facts Book, Academic Press Limited (1993), pp. 104–105 and 112–113, respectively. Anti-CD2 antibodies can be obtained from Coulter Corp. Anti-CD5 antibodies can be obtained from Becton Dickinson Immunocytometry Systems or Coulter Corp.

The CD2 antigen is a 50 kD molecular weight glycoprotein that was initially identified on T cells and NK cells and has now been shown in this invention to be expressed by circulating dendritic cells. Antibodies to this surface antigen react strongly with resting T cells. The CD2 surface antigen is divided into three regions reflecting their functional relationship. The first region, $T11_1$, is responsible for adhesion with the LFA-3 molecule and sheep erythrocyte binding. The first antibody that was produced to this region is called $T11_1$ and its clone designation is 3PTH29. The second region, $T11_2$, is an area on the CD2 antigen which does not interact with the binding domain but has been demonstrated to play a role in T cell activation in conjunction with a second antibody. The first antibody that was produced to this region is called $T11_2$ and its clone designation is 1OLD24C1. Other $T11_2$ clones are UMCD2/1E7E8, 0275, 9.6 and 7E10. The crosslinking of the $T11_2$ region with monoclonal antibodies induces unfolding of the CD2 antigen and exposure of a cryptic epitope. This cryptic epitope represents a third region, $T11_3$ or CD2R, and is expressed by activated T cells and cell-lines but only after exposure to $T11_2$ monoclonal antibodies (or others with similar traits), which induces a conformational change in structure of the CD2 antigen. The first antibody to this region was $T11_3$ and its clone name is 1 mono2A6. Other $T11_3$ clones are VIT13, G144 and L304. In preferred embodiments, $T11_2$ or $T11_2$ plus $T11_3$ antibodies are used.

In certain embodiments, prior to contacting the myeloid cells with antibodies, the myeloid cells are cultured, preferably for about 12 hours to about 36 hours, in about 5% to about 10% pooled mammal specific serum. For example, pooled human serum is used if the isolation is from human peripheral blood, and pooled pig serum is used if the isolation is from pig peripheral blood. After such culturing, antibodies, preferably anti-CD83 antibodies, can be used so as to form an antibody-dendritic cell complex. (CD83 is described in Zhou et al., J. Immunol. 154: 3821–3835 (1995); Crawford et al., Blood 80(10) Suppl. 1:192a (1992)). Anti-CD83 antibodies can be isolated as described in Zhou et al., J. Immunol. 149:735 (1992). The dendritic cells that are isolated in this embodiment can be phenotypically $CD14^-$.

The antibody-dendritic cell complex that is formed, e.g., as a result of using any of the antibodies described above, is selectively separated from the monocytes. In certain embodiments, the separation comprises contacting the antibody-dendritic cell complex and the monocytes with a matrix such that the antibody-dendritic cell complex is substantially retained by the matrix and the monocytes are substantially not retained by the matrix. Preferably, the retained antibody-dendritic cell complex is then eluted from the matrix.

In preferred embodiments, the antibody-dendritic cell complex further comprises magnetic beads, as described above. In such embodiments, separation of the antibody-dendritic complex from the monocytes preferably comprises contacting the monocytes and antibody-dendritic cell complex having the magnetic beads with a magnetic matrix such that the antibody-dendritic cell complex having the magnetic beads is substantially retained by the magnetic matrix and the monocytes are substantially not retained by the magnetic matrix. Preferably, the retained antibody-dendritic cell complex is then eluted from the matrix. The complex can be eluted, e.g., by demagnetizing the matrix, e.g., by removing the matrix from the magnetic field.

Preferably, the dendritic cells in the fourth cell population are greater than about 60% pure, more preferably greater than about 70% pure, more preferably yet greater than about 80% pure, more preferably yet greater than about 90% pure, more preferably yet greater than about 95% pure, more preferably yet greater than about 98% pure, and most preferably greater than about 99% pure. In certain embodiments, the dendritic cells in the fourth cell population are substantially unactivated. In certain embodiments, the above method further comprises the step of activating the dendritic cells in the fourth cell population, comprising culturing the dendritic cells with $T11_3$ antibodies or LFA-3 ligand.

Preferably, the monocytes in the third cell population are greater than about 70% pure, more preferably greater than about 80% pure, more preferably yet greater than about 90% pure, more preferably yet greater than about 95% pure, more preferably yet greater than about 98% pure, and most preferably greater than about 99% pure. Preferably, the monocytes in the third cell population are substantially unactivated. An advantage of the present invention is that it can produce monocytes which are unactivated. Other monocyte isolation procedures which use plastic adherence are known to rapidly induce monocyte activation. See Triglia et al., Blood 65(4):921–928 (1985).

The invention also includes a method for the enrichment of dendritic cells from the peripheral blood of a mammal comprising selecting cells from the peripheral blood which do not express antigens CD3, CD16/56 and CD19 or CD20, and which do express antigen CD2, CD5, CD83, or mixtures thereof. Preferably, cells are selected which also express antigen CD14. In certain embodiments, cells are selected which do not express antigen CD14.

The invention also includes a method for the enrichment of dendritic cells from tissue of a mammal. Tissue having mononuclear cells from a mammal is provided. The mononuclear cells are separated from the tissue. The mononuclear cells are separated into a first cell population having substantially lymphocytes and a second cell population having substantially myeloid cells. The myeloid cells are separated into a third cell population having substantially monocytes and a fourth cell population having substantially dendritic cells. The tissue can be from any part of the body of the mammal that has dendritic cells, e.g., skin or lymph nodes.

The invention also includes the products obtained from the methods described above.

The invention also includes a substantially purified population of mammalian dendritic cells wherein the dendritic cells express antigen CD14. Histogram analysis of the staining of leukocyte cell surface antigens has demonstrated that dendritic cells are $CD14^+$. By substantially purified population is meant that greater than about 80% of the cells are dendritic cells, preferably greater than about 90%, more preferably greater than about 95%, more preferably yet greater than about 98%, and most preferably greater than about 99%. In certain embodiments, the dendritic cells express antigen CD2. In certain embodiments, the dendritic cells express antigen CD5. In certain embodiments, the dendritic cells express antigen CD83.

The substantially purified dendritic cells of this invention are useful for many clinical applications, e.g., in adoptive immunotherapy (such as for use in the production of pathogen specific CTL production or in antigen specific T helper cell production), or for vaccine-therapy (such as antigen pulsed dendritic cells reinjected into the patient), or for enhanced graft acceptance. The dendritic cells of this invention are also useful in studies evaluating blood dendritic cell maturation and development; elucidation of CD2-LFA-3 signal transduction pathways; studies investigating primary immune response by antigen pulsed blood dendritic cells;

analysis of tumor immunity by tumor-antigen exposed blood dendritic cells; studies evaluating HIV-1 infectivity by dendritic cells and pathogens; comparisons of antigen uptake processing and presentation of dendritic cells, particularly as compared to monocytes; and analysis of gene expression in blood dendritic cells.

The invention further includes a kit useful for enriching for dendritic cells from blood. The kit includes anti-CD2 antibodies, anti-CD5 antibodies, anti-CD83 antibodies, or mixtures thereof. The kit also includes lymphocyte antibodies. Lymphocytes are meant to include, e.g., T cells, NK cells, B cells and mixtures thereof. Preferably, antibodies to the T cells are anti-CD3 antibodies. Other antibodies to T cells can be used, e.g., anti-CD8 antibodies. Preferably, antibodies to the NK cells are anti-CD16/56 antibodies, and antibodies to the B cells are anti-CD19 or anti-CD20 antibodies. Preferably, monoclonal antibodies are used. Preferably, instructions are provided which have information to the user regarding the use of the antibodies for enriching for dendritic cells from blood.

In certain embodiments, the kit also has magnetic beads, e.g., superparamagnetic microparticles. The magnetic beads can be complexed to the antibodies, or they can be separate. In certain embodiments, the kit has matrix material. Preferably, the matrix is provided in a column. Preferably, the matrix is capable of being magnetized by exposure to a magnetic field, e.g., the matrix can be steel wool. The kit also can include an electromagnet for use in generating a magnetic field.

The invention further includes a vaccine composition for treating cancer in a mammal, comprising a therapeutically effective amount of dendritic cells wherein the dendritic cells express antigen CD14. Preferably, the dendritic cells are treated with cancer-specific antigen so as to stimulate host immunity to the cancer when the vaccine composition is administered to a mammal.

The cancer can be any type of cancer, e.g., a solid tumor, e.g., B-cell lymphoma. Mammal is meant to include human as well as non-human mammals. Treating is meant to include, e.g., preventing, treating, reducing the symptoms of, or curing the cancer. The cancer-specific antigen can be any antigen that can be recognized by the immune system of the mammal, e.g., a cancer-specific idiotype protein. By idiotype is meant antigenic motifs formed by the combination of the variable regions of immunoglobulin heavy and light chains. Treating of the dendritic cells with the cancer-specific antigen can be by any method which results in the dendritic cells presenting the antigen so as to stimulate host immunity when the vaccine composition is administered to the mammal, e.g., by pulsing or culturing the dendritic cells in the presence of the antigen prior to administration of the vaccine composition to the mammal.

In certain embodiments the vaccine composition has a pharmaceutically acceptable carrier; in certain embodiments the vaccine composition has an adjuvant.

The invention further includes a method for treating cancer. A mammal in need of treatment for cancer is provided. A vaccine composition comprising a therapeutically effective amount of dendritic cells wherein the dendritic cells express antigen CD14, is provided. The vaccine composition is administered to the mammal such that treatment of the cancer occurs.

By therapeutically effective amount is meant that amount which is capable of at least partially preventing or reversing the symptoms of the cancer. A therapeutically effective amount can be determined on an individual basis and will be based, at least in part, on consideration of the species of mammal, the mammal's size, the dendritic cells used, the type of delivery system used and the time of administration relative to the progression of the cancer. A therapeutically effective amount can be determined by one of ordinary skill in the art employing such factors and using no more than routine experimentation.

The dendritic cells can be administered to the mammal by any method which allows the dendritic cells to reach the appropriate cells. These methods include, e.g., injection, infusion, deposition, implantation, oral ingestion or topical administration. Preferably, administration is by injection. Injections can be, e.g., intravenous, intramuscular, intradermal, subcutaneous or intraperitoneal. Single or multiple doses can be administered over a given time period, depending upon the cancer, as can be determined by one skilled in the art without undue experimentation. In certain embodiments, the injections can be given at multiple locations. Administration of the dendritic cells can be alone or in combination with other therapeutic agents.

The following non-limiting examples further illustrate the present invention.

EXAMPLES

Example 1

Isolation of Peripheral Blood Dendritic Cells and Monocytes

This example illustrates the enrichment of monocyte and dendritic cell populations from human peripheral blood.

(a) Selection (I) of Myeloid Cells

Leukocytes from a human peripheral blood sample were placed on a discontinuous Ficoll-gradient. Centrifugation separated the peripheral blood mononuclear cells (PBMCS) from the red blood cells. The PBMC population was suspended in a magnesium-free and calcium-free 2% Hanks' balanced salt solution (HBSS) at a concentration of $10^8$ cells per ml. 20 $\mu$l of directly conjugated mouse anti-human magnetic beads (anti-CD3, anti-CD16, anti-CD19) (MACS superparamagnetic microbeads conjugated with monoclonal anti-human CD3, CD16 or CD19 antibodies, obtained from Miltenyi Biotec, Auburn, Calif.), was added so as to deplete the T cell, NK cell and B cell lymphocytes. This suspension was incubated for 30 minutes at 4° C. and was then passed through a magnetic column (obtained from Miltenyi Biotec, Auburn, Calif.). The magnetic column subjected to the magnetic field retained the lymphocytes (T cells, NK cells and B cells) which were complexed with the antibody magnetic beads, and allowed elution of the antibody-magnetic-bead-negative PBMCs (monocytes and dendritic cells).

(b) Selection (I) of Monocytes and Dendritic Cells

The eluted cells from (a) were resuspended and washed in a centrifuge with a magnesium-free 2% Hanks' balanced salt solution (HBSS) twice for 10 minutes at 1200 rpms. To block Fc receptor non-specific binding of the Fc component, the washed cell population was resuspended in 10% human IgG-HBSS at $10^8$ cells per ml, and incubated for 30 minutes at 4° C. The addition of human IgG to the cell suspension blocks nonspecific interaction of the Fc component of the anti-CD2 monoclonal antibody. Human myeloid cells express Fc receptor to most immunoglobulins and most monoclonal antibodies used are of the IgG subtype. The human IgG will specifically bind human Fc receptor more than mouse, goat or calf immunoglobulins. The cell suspension was then washed twice to remove the unbound human IgG. Goat or rat anti-mouse magnetic beads (MACS superparamagnetic microbeads conjugated with monoclonal anti-mouse IgG antibodies, obtained from Miltenyi Biotec, Auburn, Calif., or from Dynal Corp., Lake Success, N.Y., were added at 100 $\mu$l per $10^9$ cells. The cell suspension was then incubated for 30 minutes at 4° C. and subsequently passed through a magnetic column (MACS) (obtained from Miltenyi Biotec). The CD2 expressing cells (dendritic cells) were retained by the magnetic beads subjected to a magnetic field as described above, while the CD2 negative cells (monocytes) passed through the magnetic field. The dendritic cells were eluted from the column by removing the column from the magnetic field and flushing with 4° C. HBSS.

The presence of dendritic cells was confirmed under light microscopic, immunofluorescent analysis and electron microscopic analysis.

(c) Selection (II) of Myeloid Cells

Peripheral blood mononuclear cells (PBMC) were isolated from anticoagulant treated blood by density centrifugation over Ficoll-Paque. The cells were resuspended in 300 $\mu$l of Buffer A: 2.5% Hanks (2.5% human serum, $Mg^{++}$ and $Ca^{++}$ free) per $1\times10^8$ cells total, and incubated for 15 minutes. A biotinylated antibody cocktail (CD3, CD19, CD16, CD56) was added to the preparation, agitated (mixed well), and incubated for 30 minutes at 4° C. After incubation the cells were washed with buffer A and centrifuged at 300×g for 10 minutes. The supernatant was decanted and the preparation was resuspended in Buffer B: 2% Hanks (2% pooled human serum, $Mg^{++}$ and $Ca^{++}$ free). The washing was repeated and the pellet was resuspended in 900 $\mu$l of 2% Hanks per 10 cells. 100 $\mu$l streptavidin microbeads per $10^8$ total cells (final volume of 1 ml per $10^8$ total cells) was added, mixed well, and incubated for 30 minutes (15 minutes minimal) at 4° C. The cells were washed once as described above and resuspended in 1 ml of buffer per $10^8$ total cells.

A depletion column was placed in Vario MACS or Super MACs (obtained from Miltenyi Biotec, Auburn, Calif.) (see below).

| Cell number | Column type | Flowresistor | MAC separator |
| --- | --- | --- | --- |
| up to $10^7$ | BS | 22G | Vario MACs Super MACs |
| up to $2 \times 10^8$ | CS | 21G | Vario MACs Super MACs |
| up to $10^9$ | D | 20G | Super MACs |

The column was filled and rinsed with 70% EtOH. The column was then rinsed twice with buffer B, and buffer A was added and incubated for 30 minutes at 37° C. After incubation, buffer A was drained, the column was rinsed twice with buffer A, and attached to a flow resistor. The preparation (1 ml per $10^8$ cells) was added on top of the depletion column and the preparation was allowed to seep into the matrix of the column.

The column was washed with buffer and the eluted population which passed through the flow resistor was collected. This population represented the enriched myeloid population which contains both dendritic cells and monocytes.

(d) Selection (II) of Monocytes and Dendritic Cells

The non-magnetic fraction from (c) was washed and centrifuged at 300×g for 10 minutes. The supernatant was decanted, and the pellet agitated. 100 $\mu$l anti-CD2 Mab ($T11_2$) was added for a final of 200 $\mu$l, mixed well, and incubated at 4° C. for 10 minutes. The cells were washed and centrifuged at 300 g×10 minutes. The cell pellet was resuspended in 500 $\mu$l buffer B. A $RS^+$ column combined with the $RS^+$ column adapter was placed in a Vario MACS or Super MACS separator. (Note: If a small number of PBMC is used, approximately $10^8$ PBMC, use a $RS^+$ column combined with the $RS^+$ column adapter in Vario MACS or Super MACS separator. Alternatively an $MS^+$ column in a mini MACS separator can be used.) The previous column used to deplete lymphocytes can be used to positively select the dendritic cells after the lymphocytes have been removed. The enrichment procedure in step (c) was repeated to select the magnetic population which represented dendritic cells. The enriched myeloid population was added and the dendritic cell/monocyte population was allowed to seep into the matrix. This column was washed with 3×500 $\mu$l with buffer A. After the wash was completed, the column was removed and buffer B was added to elute the magnetic fraction. The separation step was repeated twice to increase the purity of the dendritic cells. The enriched monocyte population found in the eluted population had minimal dendritic cell contamination.

Example 2

Alternative Method for Isolation of Peripheral Blood Dendritic Cells and Monocytes This example illustrates a variation for enrichment of monocyte and dendritic cell populations from human peripheral blood.

Prior to the lymphocyte depletion step (the Ficoll gradient step in Example 1 used to separate granulocytes and red blood cells from blood mononuclear cells (PBMC)), PBMCs were separated into two density populations by discontinuous gradient, metrizamide (Sigma Chemical Corp., St. Louis, Mo.) or One Step (Accurate Chemical and Scientific Corp., Westbury, N.Y.) centrifugation. This step separated the lymphocyte population (T cells, B cells, NK cells) from myeloid cells in bulk. The PBMCS, at a concentration of $10^7$ cells per ml, were layered over 3 ml of 14.5% metrizamide in a 15 ml conical tube, or were layered over 12.5 ml of 14.5% metrizamide in a 50 ml conical tube. This cell suspension was spun at 1800 rpm for 10 minutes at room temperature. Two cell populations were evident by light scatter, i.e., the pelleted population which represented the high density population and the buffy layer localized at the interface which represented the low density population. The two density populations were collected and washed twice with HBSS. The majority of the high density population represented T cells, B cells, NK cells and a small population of contaminating myeloid cells, while the low density population represented dendritic cells and monocytes with a small population of contaminating lymphocytes, primarily T cells with a smaller number of B cells and NK cells.

The low density population was resuspended with HBSS. Human IgG was added and incubated for 15 minutes, and anti-CD2 ($T11_2$) was added and incubated for 30 minutes. The cells were washed, and positively selected with magnetic beads as described in Example 1.

Example 3

Isolation of $CD4^+$ T Cells (or $CD8^+$ T Cells), Monocytes and Dendritic Cells for Antigen Presentation Analysis or $CD8^+$ T Cell Clonal Expansion This example illustrates the co-isolation of $CD4^+$ T cells or $CD8^+$ T cells and dendritic cells for use in clinical adoptive immunotherapy or dendritic cell T cell vaccination procedures. Adoptive immunotherapy involves the growth of antigen pathogen specific T cell clones which are reinjected back into the patient. This example demonstrates how modification of the above-described isolation method can rapidly enrich for both T cells and dendritic cells.

The procedure involves the depletion of $CD8^+$ T cells (or $CD4^+$ T cells) (depending on which T cell population is desired), NK cells and B cells, by using anti-CD8 (or anti-CD4), anti-CD16, and anti-CD19 magnetic beads (obtained from Miltenyi Biotec or Dynal Corp.). The remaining cell populations were $CD4^+$ T cells (or $CD8^+$ T cells), dendritic cells and monocytes. The monocyte population was enriched by incubating the mixture of cells with 10% human IgG HBSS for 30 minutes at 4° C., and positively selecting for all cells binding human IgG. By depleting the anti-CD8 (or anti-CD4) monoclonal antibody from the total T cell population, dendritic cells and monocytes are found in the second population. Since T cells express the CD2 antigen, enrichment with anti-CD2 of the second population yields a substantially pure T cell/dendritic cell population and elutes a substantially pure monocyte population.

Example 4

Dendritic Cell Preparation for Dendritic Cell-Based Vaccines in Human Patients

This example illustrates the isolation of dendritic cells for use in vaccines. Large numbers of peripheral blood mononuclear cells (PBMC) are collected by leukapheresis. (If only small volumes are required, the procedure described in Example 1 can be used). As described in Example 2, the PBMC enriched population is separated into low and high density populations with a 14.5% (wt/vol) metrizamide gradient. The low density population is cultured in 10% autologous human serum for 24 hours in a humidified incubator at 37° C. supplemented with 10% $CO_2$. The high density population contains a smaller percentage of immature dendritic cells which undergoes similar treatment. Both these populations are exposed to 2 μg/ml vaccinating protein (i.e., tumor specific antigen, tetanus toxoid). After 24 hours of culturing, both populations are sequentially centrifuged through 15% and 14% (wt/vol) metriazamide gradient. This centrifugation step allows depletion of contaminating lymphocytes (i.e., removal of lymphocytes expressing CD3, CD8, CD20, and CD16 antigens). If the level of contamination by lymphoctyes is minimal by visual inspection, then depletion at this level is not necessary. The dendritic cells are immunoselected with anti-CD2 ($T11_2$) monoclonal antibodies and are subsequently activated with the $T11_3$ triggering antibody. This activated dendritic cell population is cultured again for 14–18 hours in media supplemented with protein of a 25-fold higher concentration (i.e., tumor antigen, HBsAg, tetanus toxoid). After completion of this culturing phase, the dendritic cells are resuspended in 100 ml of saline which contains 5% human serum albumin. This mixture is injected into the recipient.

Example 5

Bone Marrow-Generated Dendritic Cells

This example illustrates the generation of dendritic cells from bone marrow. $CD34^+$ PBMC are positively selected by immunobead selection as previously described. This $CD34^+$ enriched population is cultured for 7–14 days in GM-CSF which induces the growth of the dendritic cell population. After a sizable number of dendritic cells are generated, they are handled in a similar fashion as the dendritic cells enriched from the peripheral blood described above.

Example 6

Skin Dendritic Cell (Langerhan's) Enrichment

This example illustrates the generation of dendritic cells from the skin. Skin is digested overnight at 4° C. with dispase in 20% RPMI and antibiotics. Epidermis is separated and cultured in PBS supplemented with trypsin and deoxyribonuclease for 15 minutes. The cellular suspension is washed and enriched for dendritic cells in a similar fashion as the dendritic cells enriched from peripheral blood described above.

Those skilled in the art will be able to ascertain, using no more than routine experimentation, many equivalents of the specific embodiments of the invention described herein. These and all other equivalents are intended to be encompassed by the following claims.

What is claimed is:

1. A substantially purified population of mammalian dendritic cells wherein said dendritic cells express an antigen selected from the group consisting of CD2 and CD5.

2. A substantially purified population of the mammalian dendritic cells of claim 1 wherein said dendritic cells further express antigen CD14.

3. The substantially purified population of mammalian dendritic cells of claim 1, wherein said dendritic cells are enriched from the peripheral blood, or tissue, of a mammal by a method, comprising:
   providing the peripheral blood, or tissue, having mononuclear cells from a mammal;
   separating said mononuclear cells from said peripheral blood or tissue;
   separating said mononuclear cells into a first cell population having substantially lymphocytes and a second cell population having substantially myeloid cells; and
   selecting a cell population which expresses an antigen specific for dendritic cells in the myeloid population, said antigen being selected from the group consisting of CD2 and CD5, thereby resulting in a third cell population having substantially monocytes and a fourth cell population having substantially dendritic cells.

4. The substantially purified population of mammalian dendritic cells of claim 3, wherein the step of separating said mononuclear cells into said first cell population and said second cell population comprises:
   contacting said mononuclear cells with antibodies against said lymphocytes so as to form an antibody-lymphocyte complex; and
   selectively separating said antibody-lymphocyte complex from said myeloid cells.

5. The substantially purified population of mammalian dendritic cells of claim 4 wherein the step of selectively separating said antibody-lymphocyte complex from said myeloid cells comprises contacting said antibody-lymphocyte complex and said myeloid cells with a matrix such that said antibody-lymphocyte complex is substantially retained by said matrix and said myeloid cells are substantially not retained by said matrix.

6. The substantially purified population of mammalian dendritic cells of claim 4 wherein said antibody-lymphocyte complex further comprises magnetic beads.

7. The substantially purified population of mammalian dendritic cells of claim 6 wherein the step of selectively separating said antibody-lymphocyte complex having said magnetic beads from said myeloid cells comprises contacting said myeloid cells and said antibody-lymphocyte complex having said magnetic beads with a magnetic matrix such that said antibody-lymphocyte complex having said magnetic beads is substantially retained by said magnetic matrix and said myeloid cells are substantially not retained by said magnetic matrix.

8. The substantially purified population of mammalian dendritic cells of claim 4, wherein said lymphocytes are selected from the group consisting of T cells, NK cells, B cells and mixtures thereof.

9. The substantially purified population of mammalian dendritic cells of claim 4 wherein said antibodies are selected from the group consisting of T cell antibodies, NK cell antibodies, B cell antibodies and mixtures thereof.

10. The substantially purified population of mammalian dendritic cells of claim 9 wherein said T cell antibodies are selected from the group consisting of anti-CD3 antibodies and anti-CD8 antibodies.

11. The substantially purified population of mammalian dendritic cells of claim 9 wherein said NK cell antibodies are anti-CD 16/56 antibodies.

12. The substantially purified population of mammalian dendritic cells of claim 9 wherein said B cell antibodies are selected from the group consisting of anti-CD19 antibodies, anti-CD20 antibodies, and mixtures thereof.

13. The substantially purified population of mammalian dendritic cells of claim 3 wherein the separating of said myeloid cells into said third cell population and said fourth cell population comprises:
   contacting said myeloid cells with antibodies against said dendritic cells so as to form an antibody-dendritic cell complex; and
   selectively separating said antibody-dendritic cell complex from said monocytes.

14. The substantially purified population of mammalian dendritic cells of claim 13 wherein said antibody-dendritic cell complex further comprises magnetic beads.

15. The substantially purified population of mammalian dendritic cells of claim 14 wherein selectively separating said antibody-dendritic cell complex having said magnetic beads from said monocytes comprises contacting said monocytes and said antibody-dendritic cell complex having said magnetic beads with a magnetic matrix such that said antibody-dendritic cell complex having said magnetic beads is substantially retained by said magnetic matrix and said monocytes are substantially not retained by said magnetic matrix.

16. The substantially purified population of mammalian dendritic cells of claim 15 further comprising eluting said antibody-dendritic cell complex from said magnetic matrix.

17. The substantially purified population of mammalian dendritic cells of claim 13 wherein said antibodies are selected from the group consisting of anti-CD2 antibodies, anti-CD5 antibodies and mixtures thereof.

18. The substantially purified population of mammalian dendritic cells of claim 13 further comprising culturing said myeloid cells prior to contacting said myeloid cells with said antibodies.

19. The substantially purified population of mammalian dendritic cells of claim 4, wherein said dendritic cells in said fourth cell population are greater than about 90% pure.

20. The substantially purified population of mammalian dendritic cells of claim 4, wherein said dendritic cells in said fourth cell population are greater than about 95% pure.

21. The substantially purified population of mammalian dendritic cells of claim 4, wherein said dendritic cells in said fourth cell population are greater than about 99% pure.

22. The substantially purified population of mammalian dendritic cells of claim 3 wherein said dendritic cells in said fourth cell population are substantially unactivated.

23. The substantially purified population of mammalian dendritic cells of claim 3 further comprising the step of activating said dendritic cells in said fourth cell population, comprising culturing said dendritic cells with $T11_3$ antibodies or the LFA-3 ligand.

24. The substantially purified population of mammalian dendritic cells of claim 3 wherein said monocytes in said third cell population are substantially unactivated.

25. The substantially purified population of mammalian dendritic cells of claim 1, wherein said dendritic cells are enriched from the peripheral blood mononuclear cells of a mammal by a method, comprising:
   providing peripheral blood mononuclear cells from a mammal;
   separating said peripheral blood mononuclear cells into a first cell population having substantially lymphocytes and a second cell population having substantially myeloid cells; and
   selecting a cell population which expresses an antigen specific for dendritic cells in the myeloid population, said antigen being selected from the group consisting of CD2 and CD5, thereby resulting in a third cell population having substantially monocytes and a fourth cell population having substantially dendritic cells.

26. The substantially purified population of mammalian dendritic cells of claim 1, wherein said dendritic cells are enriched from the myeloid cells of a mammal by a method, comprising:
   providing myeloid cells from a mammal; and
   selecting a cell population which expresses an antigen specific for dendritic cells in the myeloid population, said antigen being selected from the group consisting of CD2 and CD5, thereby resulting in a cell population having substantially monocytes and a second cell population having substantially dendritic cells.

27. The substantially purified population of mammalian dendritic cells of claim 1, where said dendritic cells are enriched from the peripheral blood mononuclear cells of a mammal by a method, comprising:
   selecting cells from said peripheral blood mononuclear cells which do not express antigens CD3, CD16/56 and CD19 or CD20, and which do express an antigen selected from the group consisting of CD2, CD5, and mixtures thereof.

28. The substantially purified population of mammalian dendritic cells of claim 13, wherein said antibodies are anti-CD2 antibodies.

29. The substantially purified population of mammalian dendritic cells of claim 25, wherein the selection of the cell population from said myeloid cells comprises:
   contacting said myeloid cells with at least one antibody against said dendritic cells so as to form an antibody-dendritic cell complex; and
   selectively separating said antibody-dendritic cell complex from said myeloid cells.

30. The substantially purified population of mammalian dendritic cells of claim 29, wherein said at least one antibody is an anti-CD2 antibody.

31. The substantially purified population of mammalian dendritic cells of claim 26, wherein said at least one antibody is an anti-CD2 antibody.

32. The substantially purified population of mammalian dendritic cells of claim 1 , wherein said dendritic cells are enriched from the myeloid cells of a mammal by a method, comprising:

providing myeloid cells from a mammal; and selecting a CD2-expressing cell population from said myeloid cells, thereby resulting in a cell population having substantially monocytes and a second cell population having substantially dendritic cells.

33. The substantially purified population of mammalian dendritic cells of claim 32, wherein the selection of the CD2-expressing cell population from said myeloid cells comprises:

contacting said myeloid cells with at least one anti-CD2 antibody so as to form an antibody-dendritic cell complex; and selectively separating said antibody-dendritic cell complex from said monocytes.

34. The substantially purified population of mammalian dendritic cells of claim 32, wherein the contacting and selectively separating steps are repeated.

35. The substantially purified population of mammalian dendritic cells of claim 32, wherein said anti-CD2 antibody binds to an area on the CD2 antigen that does not interfere with LFA-3 binding to the CD2 antigen.

36. The substantially purified population of mammalian dendritic cells of claim 32, wherein said anti-CD2 antibody binds to greater than 95% of the dendritic cells present in the peripheral blood mononuclear cells.

37. The substantially purified population of mammalian dendritic cells of claim 33, wherein the contacting and separating steps occur in about 75 min.

38. The substantially purified population of mammalian dendritic cells of claim 13, wherein said dendritic cells are enriched from the myeloid cells of a mammal by a method, comprising:

providing myeloid cells from a mammal; and selecting a cell population which expresses a dendritic cell-specific antigen selected from the group consisting of CD2 and CD5, from said myeloid cells, thereby resulting in a cell population having substantially monocytes and a second cell population having substantially dendritic cells, wherein said dendritic cells are substantially unactivated.

39. The substantially purified population of mammalian dendritic cells of claim 3, wherein said myeloid population is greater than about 80% pure.

40. The substantially purified population of mammalian dendritic cells of claim 3, wherein said antigen is CD2.

41. The substantially purified population of mammalian dendritic cells of claim 3, wherein said antigen is CD5.

42. The substantially purified population of mammalian dendritic cells of claim 25, wherein said antigen is CD2.

43. The substantially purified population of mammalian dendritic cells of claim 25, wherein said antigen is CD5.

44. The substantially purified population of mammalian dendritic cells of claim 26, wherein said antigen is CD2.

45. The substantially purified population of mammalian dendritic cells of claim 26, wherein said antigen is CD5.

46. The substantially purified population of mammalian dendritic cells of claim 3, wherein the yield of dendritic cells represents greater than about 3% of peripheral blood mononuclear cells.

47. The substantially purified population of mammalian dendritic cells of claim 25, wherein the yield of dendritic cells represents greater than about 3% of peripheral blood mononuclear cells.

48. The substantially purified population of mammalian dendritic cells of claim 26, wherein the yield of dendritic cells represents greater than about 3% of peripheral blood mononuclear cells.

* * * * *